United States Patent
Forestiere et al.

(10) Patent No.: US 9,193,922 B2
(45) Date of Patent: Nov. 24, 2015

(54) PROCESS OF DIRECT CONVERSION OF A CHARGE COMPRISING OLEFINS WITH FOUR AND/OR FIVE CARBON ATOMS, FOR THE PRODUCTION OF PROPYLENE WITH CO-PRODUCTION OF GASOLINE

(75) Inventors: Alain Forestiere, Vernaison (FR);
Vincent Coupard, Vaulx en Velin (FR);
Sylvie Lacombe, Vernaison (FR);
Sylvain Louret, Lyons (FR)

(73) Assignee: IFP ENERGIES NOUVELLES, Rueil-Malmaison Dedex (FR)

( * ) Notice: Subject to any disclaimer, the term of this patent is extended or adjusted under 35 U.S.C. 154(b) by 2127 days.

(21) Appl. No.: 11/722,300

(22) PCT Filed: Dec. 13, 2005

(86) PCT No.: PCT/FR2005/003141
§ 371 (c)(1),
(2), (4) Date: Oct. 16, 2009

(87) PCT Pub. No.: WO2006/067305
PCT Pub. Date: Jun. 29, 2006

(65) Prior Publication Data
US 2010/0036182 A1    Feb. 11, 2010

(30) Foreign Application Priority Data
Dec. 21, 2004  (FR) ...................................... 04 13680

(51) Int. Cl.
*C07C 4/06* (2006.01)
*C10G 69/12* (2006.01)
*C07C 2/10* (2006.01)
*C07C 11/06* (2006.01)

(52) U.S. Cl.
CPC ................ *C10G 69/126* (2013.01); *C07C 2/10* (2013.01); *C07C 4/06* (2013.01); *C07C 11/06* (2013.01); *C10G 2400/02* (2013.01)

(58) Field of Classification Search
CPC .............. C07C 2/00; C07C 2/02; C07C 2/04; C07C 2/06; C07C 2/08; C07C 2/12
USPC ......... 585/251, 324, 329, 651, 653, 502, 511, 585/512, 518, 519, 520, 531, 532, 533, 648, 585/649, 650; 208/142, 143, 144, 145
See application file for complete search history.

(56) References Cited

U.S. PATENT DOCUMENTS 4,392,002 A    7/1983  Cosyns et al.
4,795,844 A *  1/1989  Martindale et al. ........... 585/415
(Continued)

FOREIGN PATENT DOCUMENTS

EP    0 109 059 A1    5/1984
FR    2 492 365 A1    4/1982
FR    2 837 199 A1    9/2003

*Primary Examiner* — In Suk Bullock
*Assistant Examiner* — Sharon Pregler
(74) *Attorney, Agent, or Firm* — Millen, White, Zelano, Branigan, P.C.

(57) ABSTRACT

The invention relates to a process for production of propylene from a C4/C5 olefin cut (for example from steam cracking and/or catalytic cracking), this process comprising an optional selective hydrogenation, a selective oligomerization of the isobutenes and an oligocracking of the n-butenes.

The invention makes it possible to obtain a high conversion rate with a good propylene yield and to maximize the production of good-quality gasoline.

18 Claims, 1 Drawing Sheet

(56) References Cited

U.S. PATENT DOCUMENTS

| | | | |
|---|---|---|---|
| 6,049,017 A * | 4/2000 | Vora et al. | 585/324 |
| 6,165,439 A * | 12/2000 | Benazzi et al. | 423/713 |
| 7,161,053 B2 * | 1/2007 | Beckmann et al. | 585/530 |
| 7,262,332 B2 | 8/2007 | Duplan et al. | |
| 7,314,964 B2 | 1/2008 | Abrevaya et al. | |
| 7,579,513 B2 * | 8/2009 | Duplan et al. | 585/653 |
| 2005/0096492 A1 * | 5/2005 | Dath et al. | 585/653 |

* cited by examiner

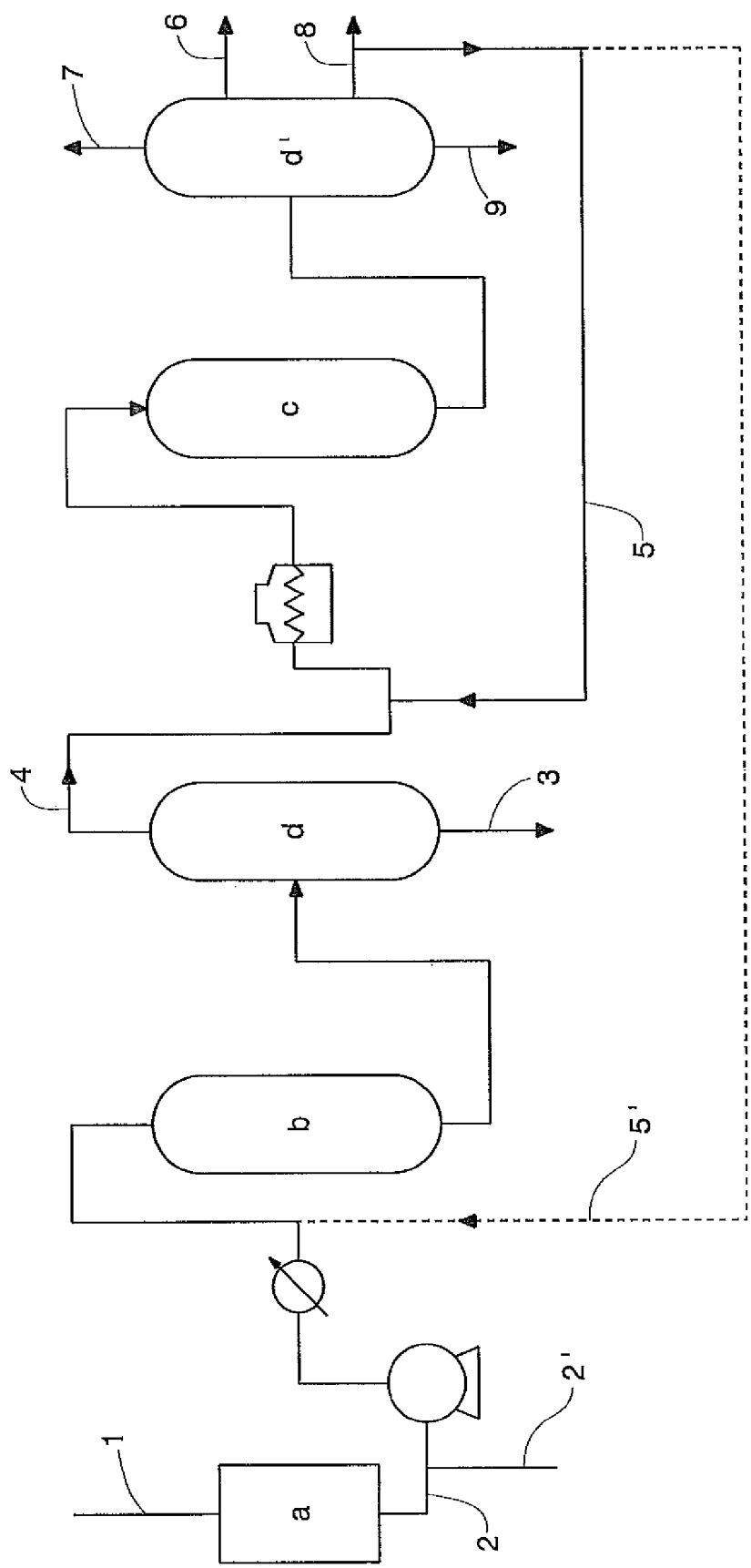

PROCESS OF DIRECT CONVERSION OF A CHARGE COMPRISING OLEFINS WITH FOUR AND/OR FIVE CARBON ATOMS, FOR THE PRODUCTION OF PROPYLENE WITH CO-PRODUCTION OF GASOLINE

FIELD OF THE INVENTION

The invention relates to a process allowing the at least partial conversion to propylene of a hydrocarbons charge comprising olefins the carbon number of which is for the most part equal to 4 or 5, this cut—which will be called C4/C5 cut in the remainder of the text—most often coming from an FCC unit or from a steam-cracking unit.

The term FCC describes the process of fluidized-bed catalytic cracking of oil fractions with a boiling point above approximately 350° C., for example a vacuum distillate, optionally deasphalted oil or an atmospheric residue.

C4/C5 olefin cuts are available in large, often surplus, quantity, in oil refineries and steam-cracking installations.

However, their recycling in refining units is problematic:
on the one hand, their recycling to steam cracking presents problems, because the yields of light olefins are lower than with paraffin cuts and they have a relatively higher tendency to form coke; and
on the other hand, their recycling to FCC would require the use of more severe conditions or specific catalysts, which would significantly modify the FCC procedure.

The charge of the process according to the invention can also comprise C4/C5, or even larger, fractions coming from a chamber or fluidized-bed coking unit, a visbreaking unit or a Fischer-Tropsch synthesis unit.

The charge can also comprise fractions of a steam-cracked gasoline.

In summary, the charge of the process according to the present invention is therefore a C4/C5 olefin cut, i.e. typically a light olefin charge, containing for the most part (i.e. more than 50%, preferably at least 60%) C4 and/or C5 olefins, whose final distillation point is generally below 320° C., most often below 250° C. Often, the olefin charge of the present invention also comprises highly unsaturated compounds, such as dienes (diolefins) specially with 4 or 5 carbon atoms (in particular butadiene) and small quantities of acetylene compounds which can have from 2 to 10 carbon atoms.

The process which is the subject of the present invention successively uses catalytic reactions of selective hydrogenation, oligomerization of the iso-olefins and oligocracking of the n-olefins.

PRIOR ART

French patent FR-B-2 608 595 describes the process of metathesis which converts an ethylene+n-butene mixture to propylene.

The process according to the invention does not use metathesis, which avoids the need to use other than C4 and C5 olefins (such as ethylene) in a large quantity, such olefins of course being able to occur as impurities. Therefore it does not require massive consumption of ethylene, a high-cost product. Moreover, if it is applied on a steam-cracking site, the process according to the invention makes it possible not only not to use ethylene as charge, but also to co-produce ethylene with the propylene. As the co-production of ethylene is typically less than that of propylene, this makes it possible to enhance the propylene-to-ethylene ratio of the steam cracker, which is in line with market trends.

The process described in the international application WO-A-01/04 237 is another process for the production of propylene in a single stage from light olefins, that may be considered to be a variant of the FCC process using a catalyst comprising a ZSM-5 zeolite. The typical operating conditions of this process are a temperature close to 600° C. and a pressure of 0.1 to 0.2 MPa (1 MPa=$10^6$ Pa=10 bar). In these conditions the propylene yield is approximately 30% and can increase up to 50% with recycling of the C4 and C5 cuts which have not reacted. A drawback of this process is that the fluidized-bed technology is costly from an investment point of view and requires relatively sensitive process control. Moreover, it leads to considerable losses of catalyst through attrition.

The process according to the invention is directed toward another type of process and does not use FCC.

In the family of single-stage oligocracking processes (i.e. where there is no prior oligomerization of the C4/C5 fractions), a process can also be mentioned which is described in the article "Production of Propylene from Low Valued Olefins", which appeared in the journal "Hydrocarbon Engineering" dated May 1999. This is a fixed-bed process in which the catalyst is a ZSM-5-type zeolite acting in the presence of steam. The temperature is close to 500° C. and the pressure is comprised between 0.1 and 0.2 MPa. The reported cycle time is of the order of 1000 hours. The catalyst is regenerated in situ and its total life, i.e. the length of time it is used in the reactor before it is renewed completely, is approximately 15 months. The reported propylene yield is approximately 40%; it could rise to 60% with recycling of the C4 and C5 cuts that did not react.

This process makes it possible to obtain a relatively high propylene yield. However, it requires the use of large quantities of steam, which is not the case in the present invention, where the desired level of partial pressure on the olefins is advantageously obtained. There is no addition of water from outside in the process according to the invention.

A process described in international application WO-A-99/29 805 and in the patents or patent applications EP-B-0 921 181 and EP-A-0 921 179 can also be mentioned. These disclose an oligocracking process using a MFI-type zeolite catalyst with a high Si/Al ratio (from 180 to 1000) to limit the hydrogen transfer reactions responsible for the production of dienes and aromatics. The temperature is close to 550° C., the pressure is close to 0.1 MPa, and the space velocity is comprised between 10 $h^{-1}$ and 30 $h^{-1}$. This process includes the possibility of using fixed-, moving- or fluidized-bed reactors. The catalyst used has a MFI-type zeolite whose Si/Al ratio (silicon/aluminium atomic ratio) is greater than or equal to 180, preferably a ZSM-5 zeolite with an Si/Al ratio comprised between 300 and 1000.

The process described in the patent application EP-A-1 195 424 can also be mentioned. This is an oligocracking process also using a MFI-type zeolite catalyst with a Si/Al ratio of 180 to 1000 or a MEL-type zeolite catalyst with a Si/Al ratio of 150 to 800, these high Si/Al ratios being required in order to limit the hydrogen transfer reactions responsible for the production of dienes and aromatics. The temperature is comprised between 500° C. and 600° C., the olefins partial pressure comprised between 0.01 MPa and 0.2 MPa, and the space velocity comprised between 5 $h^{-1}$ and 30 $h^{-1}$.

U.S. Pat. No. 6,049,017, which can be considered the closest prior art, describes a process for production of ethylene and propylene from an olefin cut comprising the following succession of stages:
a) a separation of the ethylene, the propylene, then the diolefins (for example by selective hydrogenation);
b) a separation of the n-olefins and the iso-olefins by conversion of the iso-olefins using an oxidizing agent and an acid catalyst in order to form oxygenated compounds (for example by etherification);
c) a separation of the oxygenated compounds and
d) a cracking of the n-olefins using a small-pore catalyst (for example zeolitic or preferably non-zeolitic containing a SAPO) in order to obtain ethylene and propylene.

In an alternative, it is proposed to treat part of the effluent from the separation of the oxygenated compounds by oligomerization in order to obtain a flow of olefins, which is recycled to the cracker. The aim of this stage is to eliminate paraffins from the charge entering the cracker.

The present invention also uses a unit separating n-olefins and the iso-olefins, but in a unit which does not use an oxidizing agent. The drawback of such an agent (methanol, ethanol) is that it requires a separation unit (distillation, washing with water, etc.) and poses problems of pollution or even toxicity as regards the methanol.

Moreover, the process according to the present invention leads to the formation of propylene, but also of an additional quantity of gasoline of excellent quality.

SUMMARY OF THE INVENTION

The present invention relates to a process for conversion of a C4/C5 olefin C4/C5 cut to propylene and gasoline, comprising the following succession of stages:
1) in the case where the level of diolefin and acetylene impurities is greater than 1000 ppm, selective liquid-phase hydrogenation of said cut on at least one catalyst comprising at least one metal chosen from the group formed by Ni, Pd, and Pt, deposited on a non-acid refractory oxide support, so as to obtain an effluent having an insaturates content of at most 1000 ppm;
2) selective oligomerization of the iso-olefins of at least part of the effluent from stage (1), followed by a distillation, so as to obtain a gasoline fraction and at least one remaining cut containing less than 10 wt.-% isobutenes, and
3) oligocracking of the n-olefins, working in a single stage, on at least a part of the remaining cut of stage (2), on a catalyst comprising at least one zeolite having a shape selectivity and an Si/Al atomic ratio of 50 to 500, followed by a separation in order to obtain a gasoline fraction, propylene and a residual C4/C5 cut.

The C4 and C5 olefin charge generally comes from a steam-cracking or catalytic-cracking (FCC) unit.

The aromatics-rich gasoline cut from the oligocracking stage can advantageously be mixed at least in part with the gasoline cut from the selective oligomerization in order to form a gasoline having a RON octane number of at least 94. It can also be sent at least in part to an aromatics extraction complex.

The process according to the invention finally allows a propylene yield of at least 19%, preferably greater than 22%, to be obtained.

The invention also relates to an installation which comprises:

a selective hydrogenation unit containing at least one catalyst comprising at least one metal chosen from the group formed by Ni, Pd, and Pt, deposited on a non-acid refractory oxide support, the unit being fitted with ducts for the entry of the C4/C5 olefin cut to be treated and the hydrogen and for the exit of the effluent;

a unit for selective oligomerization of the iso-olefins, comprising successively a drying unit, a desulphuration unit and a reaction unit containing at least one acid selective oligomerization catalyst, the unit being fitted with ducts for the passage of the effluents between said successive units, for the entry of at least a part of the effluent from the hydrogenation unit and for the exit of the effluent;

a distillation column separating a gasoline fraction and at least one remaining cut;

a unit for oligocracking of the n-olefins, containing a catalyst comprising at least one zeolite having a shape selectivity and an Si/Al atomic ratio of 50 to 500, fitted with ducts for the entry of at least a part of the remaining cut from the distillation of the oligomerization effluent, and for the exit of the effluent;

a distillation column separating a gasoline fraction, propylene and a residual C4/C5 cut;

a duct for recycling at least part of said residual C4/C5 cut to the oligomerization unit or to the oligocracking unit and a zone for mixing the gasoline fractions from the oligomerization and oligocracking units.

In particular in this installation, the hydrogenation unit comprises a fixed-bed reactor with descending flow of the charge, a duct conveying the obtained effluent into a second fixed-bed reactor with ascending co-current of said effluent and hydrogen.

Optionally, the installation also comprises an aromatics extraction unit fitted with a duct for the entry of the oligocracking effluent and an exit duct for the exit of the dearomatized gasoline.

FIG. 1 shows the scheme of the process and of the installation according to the invention which will allow a better understanding of the following detailed description.

The charge to be treated (1) is introduced into a selective hydrogenation unit (a) and produces an effluent (2).

A charge of another origin (2') can be added to this effluent (2), on condition that the insaturates level of said charge (2') is comprised between 10 ppm and 1000 ppm, preferably between 50 ppm and 300 ppm. Typically (2') can be a FCC gasoline not needing to be hydrotreated.

The resulting charge (2)+(2') is injected into the selective oligomerization unit (b). This selective oligomerization unit (b) produces, after separation in a distillation column (d):
at the top, a lighter hydrocarbon cut (4), constituted for the most part by C4 and C5 fractions and
at the bottom, an oligomerate (3), constituted for the most part by C8 olefins and able to contain a certain proportion of compounds up to C16.

The C4/C5 cut corresponding to the flow (4) is sent mixed with the recycling flow (5), after purging, to the oligocracking unit (c).

The oligocracking unit (c) produces, after separation in a distillation column (d'):
at the top, an ethylene-rich light cut (7);
a propylene-rich effluent (6);
an intermediate fraction (8) containing C4 and C5 hydrocarbons constituted for the most part by saturated compounds, at least a part of which fraction is recycled by the flow (5) to the entry to the oligocracking unit and at the bottom, a heavy effluent (9) comprising aromatic and olefin compounds, the boiling points of which are situated in the range of gasolines, i.e. typically from 200° C. to 250° C.

In a variant of the process according to the invention, the recycling (8) from the distillation column (d') constitutes a flow (5') which is sent to the entry to the selective oligomerization unit (b).

Of course, a variant in which a part of the fraction (8) would be recycled by the flow (5) to the entry to the oligocracking unit and another part would be recycled by the flow (5') to the entry to the oligomerization unit remains wholly within the scope of the invention.

DETAILED DESCRIPTION OF THE INVENTION

The crude charge from a steam cracker or a FCC (catalytic cracking) generally contains diene (diolefin) compounds which are poisonous to the catalysts used in oligomerization and oligocracking units.

When the level of diene and acetylene impurities is greater than 1000 ppm, the charge is treated by selective hydrogenation in order to reduce the level of impurities. Advantageously, all the charges containing more than 300 ppm of these impurities, or even more than 10 ppm, are treated.

Thus, in the case of a charge (C4/C5 olefin cut) coming from steam cracking, this stage of selective hydrogenation of the dienes and acetylenes to mono-olefins is compulsory. This selective hydrogenation can treat either the crude cut from the steam cracker, or the C4 cut after it has previously been treated in a unit used to extract compounds of diolefin type by adsorption in a solvent. This type of process for the extraction of the butadiene is known to a person skilled in the art.

In the case of a charge (C4/C5 olefin cut) coming from catalytic cracking (FCC), the selective hydrogenation stage is optional, but it makes the implementation of the downstream processes easier.

Thus, in an extremely advantageous manner, in stage (1) a C4/C5 steam-cracking olefin cut is treated and in stage (2) at least a part of the effluent from stage (1) and a C4/C5 catalytic-cracking olefin cut.

The principal objective of this first selective hydrogenation stage is to convert a the diolefins (or dienes) to mono-olefins. Only the mono-olefins can be converted to propylene according to the process of the invention. It is therefore important to maximize the mono-olefins content of the charge to be treated.

Another objective of this first stage is to purify the charge of the other impurities present, in particular the acetylene compounds, which are poisonous to the catalysts used in the downstream stages.

When the diolefins content to be treated is large, the conversion is carried out using two reactors in series, optionally with recycling of a fraction of the effluent to the entry to the selective hydrogenation unit. This recycling also allows control of the global heating of the reaction.

The insaturates content of the effluent at the end of the selective hydrogenation stage (diolefins or insaturates) is at most 1000 ppm, preferably at most 300 ppm, often comprised between 10 ppm and 1000 ppm, preferably between 50 ppm and 300 ppm.

The catalysts used in this selective hydrogenation stage are generally constituted by a metal of group VIII (typically Ni or Pd) deposited on a non-acid refractory alumina or oxide support. The external acid surface area must not be too large, in order to limit the polymerization reactions at the surface of the catalyst. The preferred support is constituted by alumina.

The metal, preferably palladium, content must be comprised between 0.1 and 5 wt.-% and preferably between 0.2 and 0.6 wt.-%. When nickel is used as metal, its content is comprised between 5 and 25 wt.-%, preferably between 7 and 20 wt.-%.

The operating conditions are chosen such that the effluent remains in the liquid state, i.e. typically from 20° C. to 150° C., under pressures ranging from 5 bar to 40 bar.

The quantity of catalyst used for the reaction is typically situated between 2 $m^3$ and 8 $m^3$ of catalyst per $m^3$ of fresh charge treated.

The hydrogen is generally introduced at a rate of 5 mol-% to 30 mol-% above stoichiometry and preferably 10% to 20% above the stoichiometric quantity.

Advantageously, the reaction is performed in a fixed-bed reactor generally with a descending flow for the principal reaction, (this is the case when there are more than 1.5 wt.-% diolefins present in the effluent to be converted) and with a catalyst preferably constituted by Pd deposited on alumina, generally with ascending co-current with the hydrogen for the finishing phase of the reaction, preferably with a catalyst constituted by Pd/Ag deposited on alumina.

This arrangement has the advantage of increasing the conversion rate.

The second stage of the process according to the invention consists of a selective oligomerization of the iso-olefins (isobutenes, isopentenes) of all of the effluent from the first stage, proceeding in two phases.

The selective oligomerization of isobutene is described in a detailed manner in the patent FR-B-2 492 365.

The first phase of the selective oligomerization consists of a drying and a desulphuration of the charge.

The two functions, drying and desulphuration, are performed in the same reactor and use sieves. These sieves are generally constituted by a series of zeolites having different pore sizes (3A, 4A, 5A, 13× zeolites) or optionally activated alumina. The sieves employed in order to carry out the drying and desulphuration are generally used in an alternating reaction-regeneration cycle.

The drying and desulphuration phase is generally carried out in liquid phase, at a temperature close to ambient temperature (20 to 70° C.), at low pressures comprised between 1 bar and 15 bar.

The regeneration phase consists of sending to the reactor a dry, hot gas, for example nitrogen, at a temperature comprised between 200° C. and 400° C.

The second phase of the oligomerization stage consists of a selective oligomerization of the iso-olefins (isobutenes, isopentenes). The selectivity of the operation consists precisely in oglomerizing the isobutenes without oligomerizing the n-olefins (n-butenes, n-pentenes).

The catalyst used in this stage is an acid catalyst, for example a catalyst of silica-alumina type, a resin or a catalyst of the solid phosphoric acid type. Preferably, the catalyst used in this stage is a catalyst of silica-alumina type such as is described in the patent FR-B-2 463 802, the silica content of which is comprised between 60 and 95 wt.-%, preferably between 70 and 90 wt.-%, and having as additive between 0.1 and 5 wt.-% zinc oxide. This is generally made up to 100% with alumina.

The operating conditions are generally (and in particular in the case of the above catalyst):

temperature comprised between 20° C. and 80° C. on entering the reactor and comprised between 50 or 65° C. and 95° C. on leaving the reactor;

pressure comprised between 10 bar and 50 bar;
volume flow rate of charge per mass unit of catalyst comprised between 0.05 h$^{-1}$ and 5 h$^{-1}$, preferably comprised between 0.1 h$^{-1}$ and 3 h$^{-1}$.

The selective oligomerization stage is generally carried out in a series of N fixed-bed reactors, each of them being followed by a cooler.

The number N chosen depends on the desired n-butene selectivity. It is typically from 2 to 4. An external recycling to the entry to these N reactors is optionally used to maintain a constant isobutene content at the entry to the process. This recycling is constituted either by the effluent taken directly on leaving the reactor, or the oligomerate recovered at the bottom of the distillation column.

The temperature of each of the N coolers is adjusted during the operation in order to compensate for the loss of activity of the catalytic system used.

Downstream of the N reactors, a separation by distillation is carried out in order to separate a gasoline fraction essentially comprising hydrocarbons ranging from C6 to C16, often composed for the most part of C5 hydrocarbons, and therefore comprising C6-C16 or C8-C16 oligomers for example, and to recover one or more remaining C4 and C5 cuts comprising essentially paraffins and C5 n-olefins and iso-olefins.

This remaining C4/C5 cut typically contains 20 to 80 wt. % olefins, for the most part light olefins with 4 and/or 5 carbon atoms. The rest of the cut is constituted by iso-olefins, essentially C5 iso-olefins, and paraffins.

The C4 iso-olefins content is generally less than 10 wt.-%.

At least one C4/C5 cut produced at the end of the selective oligomerization stage (and preferably all the remaining cut) is sent into a catalytic oligocracking unit operating in a single stage.

Typically, the catalyst used in the single-stage oligocracking unit comprises at least one zeolite having a shape selectivity, this zeolite having an Si/Al atomic ratio comprised between 50 and 500, preferably comprised between 60 and 160 and better still between 75 and 150.

Moreover, the zeolite having a shape selectivity can belong to a first group constituted by one of the following structural types: MEL, MFI, NES, EUO, FER, CHA, MFS and MWW. Preferably it is chosen from MFI (such as ZSM-5) and MEL (such as ZSM-11).

The zeolite with shape selectivity can also belong to a second group constituted by the following zeolites: NU-85, NU-86, NU-88 and IM-5.

In particular one of the following commercial ZSM-5 zeolites can be used:
CBV 28014 (Si/Al ratio: 140) and CBV 1502 (Si/Al atomic ratio: 75) from Zeolyst International, Valley Forge, Pa., 19482 USA, and
ZSM-5 Pentasil with a Si/Al 125 atomic ratio from Süd-Chemie (Munich, Germany).

One of the advantages of these zeolites presenting a shape selectivity is that their use leads to a better propylene/isobutene selectivity, i.e. a higher propylene/isobutene ratio in the effluents of said oligocracking unit.

The zeolite or zeolites can be dispersed in a matrix based on silica, zirconia, alumina or silica-alumina, the proportion of zeolite often being comprised between 15 and 90 wt.-%, preferably between 30 and 80 wt.-%.

Si/Al atomic ratios comprised in the preferred range within the framework of the invention can be obtained at the time of manufacture of the zeolite or by subsequent dealumination.

The preferred catalysts are those constituted by zeolite and a matrix.

The catalyst is generally used in a mobile bed, preferably in the form of spheres with a diameter generally comprised between 1 mm and 3 mm.

The catalyst can also be used in fixed-bed state, in which case the reactor or reactors used operate alternately in reaction then in regeneration according to the well known "swing" technique.

The regeneration phase typically comprises a phase of combustion of the carbon deposits formed on the catalyst, for example by means of an air/nitrogen mixture, of air depleted in oxygen (for example due to recirculation of fumes), or simply air.

The regeneration can optionally comprise other phases of treatment and regeneration of the catalyst which will not be elaborated on here as they are not a characteristic feature of the invention.

The catalytic oligocracking unit is usually operated in a single stage at a temperature of approximately 450° C. to approximately 580° C., with a space velocity generally comprised between 0.5 h$^{-1}$ and 6 h$^{-1}$.

The operating pressure is generally comprised between 0.1 MPa and 0.5 MPa.

The conditions of regeneration of the oligocracking catalyst generally use a temperature comprised between 400° C. and 650° C., the pressure most often being close to the oligocracking pressure.

The effluent produced by the oligocracking is distilled in order to separate the propylene and the gasoline fraction; a residual C4/C5 fraction is also obtained.

The propylene is therefore separated directly by distillation of the effluent. Optionally, a so-called superfractionation distillation column can be added, in order to treat the distilled propylene.

Generally, the propylene yield per pass in relation to the quantity of olefins contained in the fresh charge of the process is greater than 19 wt.-%, preferably greater than 22 wt.-%.

The residual C4-C5 fraction can advantageously be recycled at least in part to the entry to the oligocracking unit, and/or the entry to the selective oligomerization unit. Preferably it is recycled at least into the oligocracking stage.

The recycling flow rate of said C4/C5 cut relative to the flow rate of charge entering the selective oligomerization unit can advantageously vary in a ratio of 1 to 5 and preferably 3 to 5.

The distribution of the recycle flow rate of the C4/C5 cut from the oligocracking unit to, on the one hand, the oligocracking unit and, on the other hand, the selective oligomerization unit, is carried out according to the wishes of the operator. In particular in certain cases, the whole of this recycling flow rate can be sent to the entry to the selective oligomerization unit and in other cases, the whole of this recycling flow rate can be sent to the entry to the oligocracking unit.

The gasoline fraction produced by the oligocracking unit in a single stage is an aromatic gasoline which can be mixed completely or in part with the olefin gasoline fraction produced by the selective oligomerization unit (rich in multi-branched olefins), advantageously in order to form a gasoline with an octane number at least equal to 94 RON, or be sent in part or completely to an aromatics extraction complex in order to preferably then be mixed with the gasoline pool.

EXAMPLES

The examples will be better understood following the different flows using FIG. 1. The flow numbers which appear on the material balances are those corresponding to FIG. 1.

Example 1

The charge (1) is a crude C4 steam-cracking cut. The charge (2') is a crude C4 FCC cut.

The selective hydrogenation unit uses two reactors:

The first reactor uses a 0.3 wt.-% Pd Pd/Al2O3 catalyst, on an alumina with 69 m$^2$/g specific surface area. It operates at 50° C. adiabatically in a descending crossed bed at 30 bar absolute. For the reaction to remain in liquid phase, a recycling equal to 20 times the mass charge flow is used. The overall H2/butadiene ratio is 1.05 mole/mole.

The second reactor, called "finishing reactor", is a reactor with ascending flow, using a Pd+Ag catalyst deposited on alumina, i.e. 0.2 wt.-% Pd, and 0.1% Ag deposited on an alumina with 69 m$^2$/g BET surface area. The temperature is set at 35° C., the pressure at 26 bar.

The performance figures are given in the material balance of Table 1.

On leaving the selective hydrogenation unit, the crude FCC charge and the charge from the selective hydrogenation are mixed. The resulting mixture is dried and desulphurized on 3 A and 13× molecular sieves, marketed by Axens.

The thus-treated mixture is sent to the unit for selective oligomerization of the isobutenes. This unit operates at a global VVH of 1, on a catalyst comprised 90% of silica and 10% of alumina at a temperature comprised between 30° C. and 50° C. and a pressure of 20 bar.

A distillation column (d) separates a C4/C5-rich cut from a C8-C16 oligomers-rich gasoline cut.

A fraction of the C4/C5 cut (recycle rate 1 ton/treated ton, i.e. 50% of the mass) is used as a thermal diluent.

The oligocracking is carried out in a reactor operating at 2.8 bar absolute, at 510° C., with a PPH of 3.5 h$^{-1}$ relative to the charge entering the reactor.

A single adiabatic reactor with a descending flow in gas phase is used.

The cycle time between two successive regenerations is 48 h.

The catalyst used is comprised 30% of ZSM-5 zeolite with an Si/Al atomic ratio of 140 and 70% of gamma alumina. It is prepared in the form of spheres with a diameter of 3 mm shaped by the "oil drop" technique and it flows in a moving bed.

The C4 cut from the oligocracking unit is recycled into the oligocracking process, according to the material balance of Table 1.

The gasoline cut from the oligomerization unit has a RON of 96.5 and a MON of 84. The gasoline cut from the oligocracking unit has a RON of 96.5 and a MON of 88.5. The mixing of these two gasolines leads to a gasoline with a RON equal to 96.5 and a MON of 85.

The yield of the C3 cut is 19%. This C3 cut contains 95% propylene.

The overall yield of the gasoline cut is 43%.

TABLE 1

| kg/h | (1) | (2) | (2') | (3) | (4) | (5) | (6) | (7) | (8) | (9) |
|---|---|---|---|---|---|---|---|---|---|---|
| nC4= | 2340 | 6116 | 3556 | — | 9188 | 2681 | — | — | 202 | — |
| iC4= | 2889 | 2889 | 1524 | — | 221 | 1720 | — | — | 129 | — |
| Dienes | 3976 | 2 | 20 | — | — | — | — | — | — | — |
| Paraf | 795 | 993 | 4900 | — | 5893 | 85362 | — | — | 6425 | — |
| C1 + C2 | — | — | — | — | — | — | — | 845 | — | — |
| C3 | — | — | — | — | — | — | 3830 | — | — | — |
| C5 | — | — | — | — | — | — | — | — | 1633 | — |
| C6-C12 Aros | — | — | — | — | — | — | — | — | — | 2231 |
| Coke | — | — | — | — | — | — | — | — | — | — |
| C8 | — | — | — | 9227 | 3227 | — | — | — | — | — |
| C12 | — | — | — | 1450 | 1450 | — | — | — | — | — |
| C16 | — | — | — | — | — | — | — | — | — | — |
| C20 | — | — | — | 22 | 22 | — | — | — | — | — |
| Total | 10000 | 10000 | 10000 | 4698 | 20000 | 85065 | 3830 | 845 | 8390 | 2231 |

Example 2

The data are the same as those of Example 1, with the exception of the following points:
The charge (1) is a crude C4 steam-cracking cut.
The charge (2') is a crude, C4 FCC cut.
The recycling (5) involves a fraction of the C4 and C5 cuts as given in the material balance of Table 2.
The RON of the oligomerate is still 96.5.
The overall C3 cut yield is 22%.
The overall yield of the gasoline cut is 38%.

TABLE 2

| kg/h | (1) | (2) | (2') | (3) | (4) | (5) | (6) | (7) | (8) | (9) |
|---|---|---|---|---|---|---|---|---|---|---|
| nC4= | 2340 | 6116 | 3556 | — | 9188 | 3328 | — | — | 263 | — |
| iC4= | 2889 | 2889 | 1524 | — | 221 | 2136 | — | — | 169 | — |

TABLE 2-continued

| kg/h | (1) | (2) | (2') | (3) | (4) | (5) | (6) | (7) | (8) | (9) |
|---|---|---|---|---|---|---|---|---|---|---|
| Dienes | 3976 | 2 | 20 | — | — | — | — | — | — | — |
| Paraf | 795 | 993 | 4900 | — | 5893 | 82371 | — | — | 6507 | — |
| n + i C5= | — | — | — | — | — | 1633 | — | — | 129 | — |
| Cy | — | — | — | — | — | 1436 | — | — | 113 | — |
| C5 Dienes Inerts | — | — | — | — | — | — | — | — | — | — |
| C1 + C2 | — | — | — | — | — | 1558 | — | — | 123 | — |
| C3 | — | — | — | — | — | — | — | 975 | — | — |
| C6-C12 Aros | — | — | — | — | — | — | 4423 | — | — | — |
| Coke | — | — | — | — | — | — | — | — | — | 2576 |
| C8 | — | — | — | — | — | — | — | — | — | — |
| C12 | — | — | — | 3227 | 3227 | — | — | — | — | — |
| C16 | — | — | — | 1450 | 1450 | — | — | — | — | — |
| C20 | — | — | — | 22 | 22 | — | — | — | — | — |
| Total | 10000 | 10000 | 10000 | 4698 | 20000 | 92461 | 4423 | 975 | 7304 | 2576 |

Example 3

The data of Example 3 are the same as those of Example 1, with the exception of the following points:

The charge (1) is a crude C4 steam-cracking cut.
The charge (2') is a crude C4 FCC cut
The recycling (5') is sent to the selective oligomerization unit.
The cycle time of the oligocracking unit is extended to 72 h. This recycling (5') now involves a fraction of the C4 and C5 cuts as shown in the material balance of Table 3.
The overall C3 cut yield is 22%.
The conversion rate of the C4 olefins to the C3 cut is 47%.
The RON of the oligomerate changes to 94.5 and the MON to 82.

Example 4

The data of Example 4 are the same as those of Example 1, with the exception of the following points:

The charge (1) is a crude C4 steam-cracking cut.
The charge (2') is a mixture of a crude C4 FCC cut, a crude C5 FCC cut and a crude C5 steam-cracking cut which has also undergone a treatment to eliminate the dienes, similar to that described for the C4 cut.
The recycling (5) is sent to the oligocracking unit.
The cycle time of the oligocracking unit is 48 h. This recycling (5) now involves a fraction of the C4 and C5 cuts as defined in the material balance of Table 4.
The cycle time of the oligocracking unit is 48 h.
The overall C3 cut yield is 28%.
The conversion rate of the C4-C5 olefins to the C3 cut is 42%.

TABLE 3

| kg/h | (1) | (2) | (2') | (3) | (4) | (5) | (6) | (7) | (8) | (9) |
|---|---|---|---|---|---|---|---|---|---|---|
| nC4= | 2340 | 6116 | 3556 | — | 11607 | 2546 | — | — | 206 | — |
| iC4= | 2889 | 2889 | 1524 | — | 302 | 1634 | — | — | 132 | — |
| Dienes | 3976 | 2 | 20 | — | — | — | — | — | — | — |
| Paraf | 795 | 993 | 4900 | — | 84841 | 78948 | — | — | 6401 | — |
| n + i C5= | — | — | — | — | 1249 | 1249 | — | — | 101 | — |
| Cy | — | — | — | — | 30 | 30 | — | — | 2 | — |
| C5 Dienes Inerts | — | — | — | — | — | — | — | — | — | — |
| C1 + C2 | — | — | — | — | 2011 | 2011 | — | — | 163 | — |
| C3 | — | — | — | — | — | — | — | 807 | — | — |
| C6-C12 Aros | — | — | — | — | — | — | 3658 | — | — | — |
| Coke | — | — | — | — | — | — | — | — | — | 2131 |
| C8 | — | — | — | — | — | — | — | — | — | — |
| C12 | — | — | — | 4385 | — | — | — | — | — | — |
| C16 | — | — | — | 1970 | — | — | — | — | — | — |
| C20 | — | — | — | 22 | — | — | — | — | — | — |
| Total | 10000 | 10000 | 10000 | 6378 | 100041 | 86419 | 3658 | 807 | 7007 | 2131 |

The RON of the oligomerate changes to 94.5 and the MON to 82.

TABLE 4

| kg/h | (1) | (2) | (2') | (3) | (4) | (5) | (6) | (7) | (8) | (9) |
|---|---|---|---|---|---|---|---|---|---|---|
| nC4= | 2340 | 6116 | 3556 | — | 9188 | 7133 | — | — | 1259 | — |
| iC4= | 2889 | 2889 | 1524 | — | 221 | 4577 | — | — | 808 | — |
| Dienes | 3976 | 2 | 20 | — | — | — | — | — | — | — |
| Paraf | 795 | 993 | 4900 | — | 5893 | 42168 | — | — | 7441 | — |
| n + i C5= | — | — | 12500 | — | 12500 | 3499 | — | — | 618 | — |
| Cy | — | — | 3000 | — | 3000 | 84 | — | — | 15 | — |
| C5 Dienes Inerts | — | — | — | — | — | — | — | — | — | — |
| C1 + C2 | — | — | 4500 | — | 4500 | 28316 | — | — | 4997 | — |
| C3 | — | — | — | — | — | — | — | 2459 | — | — |
| C6-C12 Aros | — | — | — | — | — | — | 11151 | — | — | — |
| Coke | — | — | — | — | — | — | — | — | — | 6495 |
| C8 | — | — | — | — | — | — | — | — | — | — |
| C12 | — | — | — | — | — | — | — | — | — | — |
| C16 | — | — | — | 3227 | — | — | — | — | — | — |
| C20 | — | — | — | 1450 | — | — | — | — | — | — |
|  | — | — | — | 22 | — | — | — | — | — | — |
| Total | 10000 | 10000 | 30000 | 4698 | 35302 | 85777 | 11151 | 2459 | 15137 | 6495 |

The invention claimed is:

1. A process for conversion of a C4/C5 olefin cut to propylene and gasoline, said C4/C5 olefin cut containing iso-olefins and n-olefins, said process comprising the following succession of stages:
   1) If said C4/C5 olefin cut contains greater than 1000 ppm of diolefinic and acetylenic impurities, conducting selective liquid phase hydrogenation with at least one catalyst comprising at least one metal chosen from Ni, Pd, and Pt, deposited on a non-acid refractory oxide support to obtain an effluent comprising said impurities of at most 1000 ppm,
   2) Drying and desulphurization followed by selective oligomerization of the iso-olefins with an acid catalyst comprising silica-alumina,
   3) Conducting distillation to obtain a gasoline fraction and at least one remaining cut containing the n-olefins and less than 10 wt % iso-olefins,
   4) Subjecting at least a part of the n-olefins in the remaining cut to oligocracking in a single stage with at least one shape selective zeolite catalyst comprising a Si/Al atomic ratio of 50 to 500 to produce an oligocracked stream, and
   5) Separating the oligocracked stream to obtain a second gasoline fraction, propylene, and a residual C4/C5 olefin cut.

2. A process according to claim 1, wherein the selective oligomerization catalyst comprises between 60 and 95 wt. % silica and an additive between 0.1 and 5 wt. % zinc oxide.

3. A process according to claim 1, wherein the selective oligomerization stage operates at:
   a temperature between 20° C. and 95° C.;
   a pressure between 10 bar and 50 bar; and
   a volume flow rate of charge per mass unit of catalyst between 0.05 h$^{-1}$ and 5 h$^{-1}$.

4. A process according to claim 1, wherein said shape selective zeolite oligocracking catalyst comprises a Si/Al ratio between 75 and 150.

5. A process according to claim 1, wherein the zeolite catalyst in the oligocracking stage is a MEL, MFI, NES, EUO, FER, CHA, MFS or MWW.

6. A process according to claim 5, wherein in which the zeolite is ZSM-5.

7. A process according to claim 1, wherein the zeolite catalyst in the oligocracking stage is a NU-85, NU-86, NU-88 or IM 5.

8. A process according to claim 1, wherein the oligocracking stage is conducted in a moving bed with the zeolite catalyst in the form of spheres having a diameter between 1 and 3 mm.

9. A process according to claim 1, wherein residual C4/C5 olefin cut from the oligocracking stage is recycled at least in part to the selective oligomerization stage.

10. A process according to claim 1, wherein residual C4/C5 olefin cut from the oligocracking stage is recycled at least in part to the oligocracking stage.

11. A process according to claim 1, wherein the residual C4/C5 olefin cut from the oligocracking stage is recycled at least in part into the oligocracking stage, and/or into the selective oligomerization stage with a flow rate ratio relative to a charge entering the selective oligomerization stage of 1 to 5.

12. A process according to claim 1, further comprising mixing the gasoline fraction from the selective oligomerization stage with the gasoline fraction from the oligocracking stage so as to obtain a gasoline with a RON at least equal to 94.

13. A process according to claim 1, wherein the gasoline fraction from the oligocracking stage is subjected, at least in part, to an extraction of the aromatics.

14. A process according to claim 1, wherein said C4/C5 olefin cut is from steam cracking and is treated in stage (1) and in stage (2) at least a part of the effluent from the stage (1) and a C4/C5 olefin cut from catalytic cracking are subjected to said selective oligomerization.

15. A process according to claim 1, wherein said at least one selective liquid phase hydrogenation catalyst comprises Pd on an alumina support.

16. A process according to claim 9, wherein the residual C4/C5 olefin cut from the oligocracking stage is recycled at least in part to the oligocracking stage.

17. A process according to claim 1, wherein the original C4/C5 olefin cut has more than 1000 ppm of diolefinic and acetylenic impurities, said cut being then subjected to said selective liquid phase hydrogenation.

18. A process according to claim 2, wherein the selective oligomerization catalyst comprises between 70 and 90 wt. % silica.

\* \* \* \* \*